US012734407B1

(12) United States Patent
Lu

(10) Patent No.: US 12,734,407 B1
(45) Date of Patent: Sep. 15, 2026

(54) TREADMILL CONTROL METHOD, TREADMILL, ELECTRONIC DEVICE, AND STORAGE MEDIUM

(71) Applicant: Shenzhen Yugong Technology Co., Ltd., Shenzhen (CN)

(72) Inventor: Feng Lu, Shenzhen (CN)

(73) Assignee: Shenzhen Yugong Technology Co., Ltd., Shenzhen (CN)

( * ) Notice: Subject to any disclaimer, the term of this patent is extended or adjusted under 35 U.S.C. 154(b) by 0 days.

(21) Appl. No.: 19/357,588

(22) Filed: Oct. 14, 2025

(30) Foreign Application Priority Data

Jul. 28, 2025 (CN) ........................ 202511040846.2

(51) Int. Cl.
*A63B 24/00* (2006.01)
*A63B 22/02* (2006.01)
*G16H 40/67* (2018.01)

(52) U.S. Cl.
CPC ........ *A63B 24/0087* (2013.01); *A63B 22/025* (2015.10); *A63B 24/0075* (2013.01); *G16H 40/67* (2018.01)

(58) Field of Classification Search
CPC ...................................................... G06N 20/00
See application file for complete search history.

(56) References Cited

U.S. PATENT DOCUMENTS

2008/0182727 A1 7/2008 Uang
2009/0036272 A1 2/2009 Yoo
2010/0041000 A1* 2/2010 Glass ....................... G09B 5/02 434/179
2010/0210418 A1 8/2010 Park
2012/0040798 A1 2/2012 Yu
2016/0284349 A1* 9/2016 Ravindran ............ G10L 15/285
2017/0157459 A1 6/2017 Chen et al.
2019/0192915 A1 6/2019 Wei et al.
2022/0339504 A1* 10/2022 Intonato ............... A63B 22/025
2025/0312652 A1* 10/2025 Brammer ........... A63B 24/0075

OTHER PUBLICATIONS

Pereira, H. et al., "Architecture to Recreate Immersive Scenarios for Practicing Sports in Gyms," Proc. of the 9th Intl. Conf. on Smart City Applications (2024) pp. 11-20. (Year: 2024).*

(Continued)

*Primary Examiner* — Brian M Smith

(57) ABSTRACT

A treadmill control method is applied to controlling a treadmill and includes obtaining a the target user's training objective information, user health data, and static physiological data; collecting the target user's dynamic physiological data through a smart wearable device; generating instruction language based on the training objective information, the user health data, the static physiological data, and the dynamic physiological data to obtain a natural language instruction; inferencing and parsing the natural language instruction based on a pre-adapted target large language model to obtain user profile parsing information; generating a treadmill control strategy adapted to the target user based on the user profile parsing information using a pre-trained decision-making agent; and controlling the treadmill's operating state based on the treadmill control strategy to provide personalized operating modes for different users.

13 Claims, 2 Drawing Sheets

(56) References Cited

OTHER PUBLICATIONS

Bhardwaj, A. et al., “Flexi-Fit: AI Based Fitness Trainer,” 3rd Intl. Conf. on Disruptive Technologies (May 13, 2025) pp. 1497-1501. (Year: 2025).*

Liao, P. et al, “Personalized HeartSteps: A Reinforcement Learning Algorithm for Optimizing Physical Activity,” Proc. of the ACM on Interactive, Mobile, Wearable, and Ubiquitous Technologies (Mar. 2020) 21 pp. (Year: 2020).*

* cited by examiner

TREADMILL CONTROL METHOD, TREADMILL, ELECTRONIC DEVICE, AND STORAGE MEDIUM

CROSS REFERENCE TO RELATED APPLICATIONS

This application claims priority benefits to Chinese Patent Application No. 2025110408462, filed on Jul. 28, 2025, the contents of which are incorporated herein by reference.

TECHNICAL FIELD

The present disclosure relates to the technical field of sports equipment, and in particular to a treadmill control method, a treadmill, an electronic device, and a storage medium.

BACKGROUND

As a crucial piece of equipment in the fitness industry, treadmills have been widely adopted in both gym and home fitness settings. In the field of fitness, how to leverage intelligent methods to help users better utilize treadmills to achieve their ideal fitness results has become an important research direction.

Although treadmills in the related art offer basic functions such as speed adjustment and incline control, users often face several challenges during operation. First, users need to set treadmill parameters appropriately based on their physical conditions and fitness goals, which can be difficult for those lacking fitness knowledge. Second, even for users with some fitness expertise, it is challenging to consistently maintain control over key metrics such as pace and heart rate during running, so as to ensure optimal workout effectiveness. Clearly, current treadmill technology falls short in meeting users' personalized training needs. These limitations hinder the effective application of treadmills in the fitness domain.

SUMMARY

The first aspect of the embodiments of the present disclosure provides a treadmill control method configured to control a treadmill equipped with a smart wearable device. The method includes: obtaining training objective information, user health data, and static physiological data of a target user; collecting, by the smart wearable device, dynamic physiological data of the target user; generating instructional language based on the training objective information, the user health data, the static physiological data, and the dynamic physiological data to obtain a natural language instruction; performing, by a pre-adapted target large language model, inferencing and parsing of the natural language instruction to obtain user profile parsing information; generating, by a pre-trained decision-making agent, a treadmill control policy adapted to the target user based on the user profile parsing information; controlling an operating state of the treadmill based on the treadmill control policy.

The second aspect of the embodiments of the present disclosure provides a treadmill configured to be controlled by the treadmill control method described above.

The third aspect of the embodiments of the present disclosure provides an electronic device, including: a memory and a processor. The memory stores a computer program, and the processor is configured to implement the treadmill control method described above.

The fourth aspect of the embodiments of the present disclosure provides a computer-readable storage medium. The computer-readable storage medium stores a program, and the program is executed by a processor to implement the treadmill control method described above.

BRIEF DESCRIPTION OF THE DRAWINGS

The foregoing and/or additional aspects and advantages of the present disclosure may become apparent and readily understood from the description of the embodiments in conjunction with the following figures.

DETAILED WAY

Figure 1:
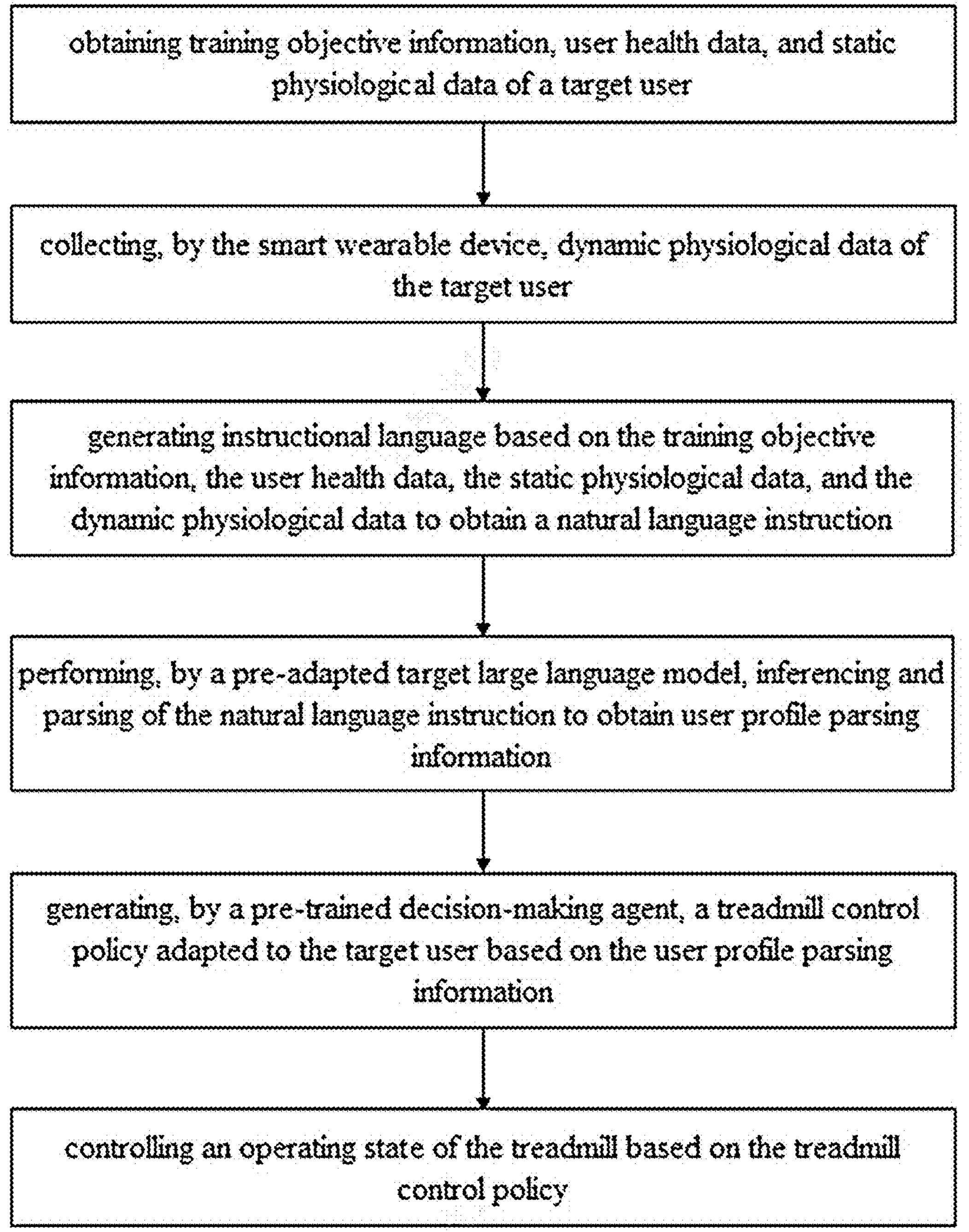
FIG. 1 is a flow chart of a treadmill control method according to some embodiments of the present disclosure.

The following describes the embodiments of the present disclosure in detail. Examples of the embodiments are illustrated in the accompanying drawings, where identical or similar reference numerals throughout indicate identical or similar elements or elements having identical or similar functions. The embodiments described below with reference to the accompanying drawings are illustrative and intended solely to explain the present disclosure and are not to be construed as limiting the present disclosure.

In the description of the present disclosure, "several" means one or more, "many" means two or more, "greater than," "less than," and "exceed" are exclusive of the number itself, while "above," "below," and "within" are inclusive of the number itself. The use of terms such as "first" and "second" is solely for the purpose of distinguishing technical features and should not be construed to indicate or imply relative importance, or to implicitly indicate the number or order of the indicated technical features.

In the present disclosure, the terms "one embodiment," "some embodiments," "illustrative embodiments," "example," "specific example," or "some examples" means that the specific features, structures, materials, or features described in connection with that embodiment or example are included in at least one embodiment or example of the present disclosure. In the present disclosure, these terms do not necessarily refer to the same embodiment or example. Furthermore, the specific features, structures, materials, or features described herein may be combined in any suitable manner in any one or more embodiments or examples. The identification of specific steps in the description of the present disclosure does not imply a limitation on the order or execution logic of the steps. The order and logic of the execution of the steps should be inferred from the description of the embodiments.

Treadmills, as an important piece of fitness equipment, have been widely used in gyms and home fitness settings. With the rapid development of artificial intelligence (AI), various industries are actively exploring how to apply AI technology to specific product functions to enhance user experience and product performance. In the fitness field, using intelligent means to help users better utilize treadmills to achieve their desired fitness results has become a key research direction.

While treadmills in the related art offer basic functions such as speed and incline adjustment, users often face numerous challenges during use. First, users need to appropriately set treadmill parameters based on their physical condition and fitness goals, which can be challenging for users lacking fitness knowledge. Second, even for users with some fitness knowledge, it is challenging to consistently maintain control over key metrics such as pace and heart rate during running, so as to ensure optimal workout effectiveness. In addition, user experience of treadmills is relatively basic. It is often devoid of personalized and intelligent guidance, making it inadequate for accommodating the wide range of user requirements.

The technical problems in the related art include the following.

The main drawback in the related treadmill technology lies in the difficulty users face in achieving optimal treadmill performance. Although treadmills have basic functions such as speed and incline adjustment, users often lack relevant fitness knowledge and are unable to accurately set and adjust these parameters for optimal fitness results. Furthermore, users struggle to monitor and adjust their physical condition, such as key indicators like heart rate and blood pressure, while running. This can lead to poor training results and even health risks.

Treadmills in the related art are unable to provide personalized training plans based on users' individual physical condition, health features, and training objectives. Users must independently discover their own running style and parameter settings, which is unrealistic for most of them without professional fitness guidance. Therefore, treadmills in the related art are significantly inadequate in meeting user needs.

Treadmills in the related art also lack intelligent guidance. Users cannot receive real-time feedback and adjustment suggestions during their run, nor can they dynamically adjust the treadmill's operating state based on their current physical condition. Treadmills without intelligent guidance make it difficult for users to achieve scientific and efficient fitness training. As can be seen, treadmill technology in the related art has significant shortcomings in areas such as personalized training program development, real-time physical condition monitoring and feedback, intelligent guidance, thus affecting user experience. These issues limit the effective application of treadmills in the fitness field and affect user satisfaction. Therefore, developing an intelligent treadmill that can address these issues has become an important direction in the fitness equipment field.

The present disclosure aims to address at least one of the technical problems existing in the related art. To this end, the present disclosure proposes a treadmill control method, a treadmill, an electronic device, and a storage medium that can provide personalized operation modes for different users.

The following is a further explanation based on the accompanying drawings.

As illustrated in FIG. 1, a treadmill control method according to some embodiments of the present disclosure is applied to control a treadmill equipped with a smart wearable device. The treadmill control method may include the following operations.

Operation S101 includes obtaining training objective information, user health data, and static physiological data of a target user.

Operation S102 includes collecting, by a smart wearable device, dynamic physiological data of the target user.

Operation S103 includes generating instructional language based on the training objective information, the user health data, the static physiological data, and the dynamic physiological data to obtain a natural language instruction.

Operation S104 includes performing, by a pre-adapted target large language model, inferencing and parsing of the natural language instruction to obtain user profile parsing information.

Operation S105 includes generating, by a pre-trained decision-making agent, a treadmill control policy adapted to the target user based on the user profile parsing information.

Operation S106 includes controlling an operating state of the treadmill based on the treadmill control policy.

The treadmill control method of the embodiments aims to provide users with a personalized exercise experience, which embodies the ingenious approach of adapting to individual user needs. By applying the target large language model and the decision-making agent to the field of exercise analysis, a customized treadmill control policy can be generated based on the unique needs and physical conditions of different users. This personalized service is reflected not only in the precise setting of exercise parameters but also in real-time companionship and intelligent guidance during exercise. For example, timely encouraging voice feedback or suggestions for users' plan adjustments can be provided based on user performance and physical responses, allowing users to experience supportive interaction provided by the intelligent device during their exercise, thereby boosting motivation and long-term exercise adherence. This eliminates the need for runners to engage in excessive exercise or acquire specialized fitness knowledge. It functions as a full-time personal trainer by side, dynamically optimizing their training plans based on changes in their physical conditions.

In some embodiments, operation S101 includes obtaining training objective information, user health data, and static physiological data of a target user.

Obtaining the target user's training objective information is the primary operation in developing a personalized treadmill plan. In some embodiments, this can be accomplished by guiding the user to complete a comprehensive fitness goal questionnaire on a mobile app or other devices associated with the treadmill. This questionnaire includes the primary purpose for using the treadmill, such as weight loss, muscle building, improving cardiorespiratory endurance, preparing for a marathon, or improving overall health. Furthermore, users can define specific fitness goals, such as a target number of kilograms within three months or improving running endurance to sustain a continuous run for a set duration. This detailed goal information may serve as an important basis for subsequently generating a treadmill control strategy.

Collecting user health data is a key operation in ensuring safe and effective training. This data includes a user's medical history, such as heart disease, high blood pressure, asthma, knee problems, or other health issues that may affect exercise. It also provides information about the users' current physical condition, such as any chronic pain or recent injury recovery. This information can be entered manually, or more accurate data can be sourced automatically from their electronic health records, if access is granted. Furthermore, users can be asked about their general health habits, such as sleep quality, dietary habits, and daily activity levels. This information helps to comprehensively assess their health and support the development of an appropriate treadmill training plan.

The collection of static physiological data provides basic physiological parameters for treadmill exercise. This includes basic information such as a user's height, weight, gender, age, and body mass index (BMI). This data can be entered by the user through a mobile app or other terminal devices or automatically collected from devices such as smart body fat scales. For example, the user's height and weight can be configured to calculate calorie burn rate and determine treadmill settings, such as track length and handrail height, that are appropriate for body size. In addition, the user's body composition information, such as body fat percentage and muscle mass, can also serve as a reference for optimizing treadmill training plans, helping to determine whether a training mode focusing on fat loss or muscle gain is appropriate.

In some embodiments, operation S102 includes collecting, by the smart wearable device, dynamic physiological data of the target user.

Firstly, the smart wearable device can include a variety of devices, such as smart watches/bracelets, heart rate monitors, and smart insoles, which can monitor various physiological indicators of the user during exercise in real time. For example, smart watches/bracelets can accurately measure the user's heart rate, blood pressure fluctuations, and cadence and stride length. Heart rate monitors can provide more detailed heart rate data, including heart rate variability, which is very useful for assessing exercise intensity and physical fatigue. Smart insoles can monitor the user's plantar pressure distribution, gait features, and contact and air time. This rich dynamic physiological data provides comprehensive real-time information for subsequent personalized control strategies.

Secondly, the data collected by the smart wearable device helps reflect trends in the user's exercise status. In addition to basic physiological indicators, these devices also record temporal exercise data, such as the duration of sustained exercise and the duration spent within different intensity zones. By integrating this time series data, the decision-making agent can analyze the user's exercise patterns and endurance trends. For example, if the data shows a significant drop in speed and an increase in heart rate in the second half of each run, the intelligent system might appropriately reduce the intensity of subsequent training sessions or recommend increasing rest intervals, thereby helping the user gradually improve endurance and optimize training results.

When collecting dynamic physiological data from the target user via smart wearable devices, a time interval method and threshold overload method can be configured to ensure that the transmission of data does not consume excessive network resources while effectively monitoring changes in key physiological indicators.

Regarding the time interval method, according to some embodiments, operation S102 which includes collecting, by the smart wearable device, dynamic physiological data of the target user, may further include the following.

The smart wearable device collects physiological data from the target user once every sampling interval to update the dynamic physiological data.

The sampling interval method involves setting a time interval at which physiological data is collected and transmitted. This method effectively controls the frequency of data transmission, thereby reducing network resource usage.

The sampling interval can be fixed. For example, heart rate data can be collected every 10 seconds. The advantage of a fixed sampling interval lies in that it provides evenly distributed data points, facilitating periodic data analysis and long-term trend observation. This setting is suitable for monitoring under stable conditions, such as during low- to medium-intensity continuous running, ensuring stable data acquisition, continuity, and integrity.

However, in some cases, a flexible sampling interval is more appropriate. For example, when a user is engaged in high-intensity interval training, where exercise status changes rapidly, the sampling interval can be shortened, such as collecting data every 5 seconds, to more promptly capture changes in physiological data. Conversely, when the user is engaging in low-intensity exercise or resting, the sampling interval can be appropriately extended, such as every 15 or 20 seconds, to reduce data volume and conserve network resources.

In addition, the sampling interval can be flexibly adjusted based on the user's individualized needs and health status. For example, users with special health needs, such as heart disease, may need to monitor their heart rate more closely; in this case, the sampling interval can be set to a shorter interval. Meanwhile, healthy users can use a relatively longer sampling interval during regular exercise.

Due to the programmable nature of smart wearable devices, the sampling interval in the embodiments of the present disclosure needs to be determined based on the specific type of physiological data and exercise scenario. For example, for heart rate monitoring during treadmill exercise, if the user's exercise intensity is low, the sampling interval can be appropriately extended, such as every 15 seconds. However, for high-intensity interval training, more frequent data collection, such as every 5 seconds, may be required to more accurately capture heart rate changes.

This flexibility to set sampling intervals enables smart wearable devices to optimize data collection and transmission efficiency while ensuring effective monitoring of changes in key physiological indicators, reducing network resource consumption, extending battery life, and providing users with more personalized monitoring services.

Regarding a threshold overload method, according to some embodiments, operation S102 of collecting, by the smart wearable device, dynamic physiological data of the target user, may include the following operations: performing, by the smart wearable device, a physiological data monitoring operation on the target user to determine real-time monitored physiological data; collecting real-time monitored physiological data in response to the real-time monitored physiological data meeting a preset threshold setting condition; updating the dynamic physiological data of the target user based on the real-time monitored physiological data.

The threshold overload method involves setting thresholds for one or more key physiological data. Data collection and transmission occurs only when the physiological data exceeds or falls below these thresholds. This method can further reduce unnecessary data transmission by only transmitting data when significant changes in physiological data occur, thereby conserving network resources.

For example, for heart rate monitoring, an upper threshold and a lower threshold can be set. If the user's heart rate fluctuates within a normal range, the system may not transmit data frequently. Only when the heart rate exceeds an upper threshold (e.g., 180 beats/minute) or falls below a lower threshold (e.g., 50 beats/minute) will the system trigger data transmission and alert the user or take an appropriate action.

The threshold setting needs to be customized based on users' health status and exercise goals. For example, for users with a history of heart disease, the upper heart rate threshold may need to be set lower to ensure user safety. Professional athletes, on the other hand, may require a higher threshold to accommodate their high-intensity training needs.

In some embodiments, the time interval method and the threshold overload method can be combined to achieve better results. For example, a basic time interval can be set (e.g., data collection every 10 seconds) and a threshold for key physiological data can be set simultaneously. Under normal circumstances, the system collects and transmits data at the time interval; however, if the physiological data exceeds the threshold, the system immediately collects and transmits the data without waiting for the next time interval.

This combined approach ensures real-time data and monitoring of changes in key physiological indicators while minimizing network resource consumption. For example, during a regular running workout, heart rate data is transmitted every 10 seconds. However, if the user's heart rate suddenly rises to near the preset upper threshold, the system immediately transmits the current heart rate data so that the treadmill speed or incline can be adjusted in a timely manner to ensure user safety.

By employing the time interval method and the threshold overload method, smart wearable devices can optimize data collection and transmission strategies, reduce network resource usage, and improve overall system efficiency while ensuring effective monitoring of changes in key physiological indicators.

In some embodiments, operation S103 includes generating instructional language based on the training objective information, the user health data, the static physiological data, and the dynamic physiological data to obtain a natural language instruction.

The core task of this operation is to integrate multi-dimensional user data into a structured natural language text for subsequent large language model processing. This operation parses data from various channels, including training objectives, health status, and basic physiological data manually entered by the user, as well as dynamic physiological data monitored in real time by the smart wearable device. Then, using a preset sentence template or natural language generation algorithm, these scattered data points are woven into a fluent, coherent, and informative natural language instruction.

In some embodiments, an automated instruction generation module can first be constructed. This instruction generation module is capable of receiving and parsing structured user data from various channels, including basic user information, health status, training objectives, and real-time monitored physiological data. The instruction generation module has multiple pre-set templates optimized for different user profiles and training scenarios. For example, for users aiming to lose weight, a template might highlight low-intensity aerobic exercise and long exercise durations; for those aiming to improve cardiopulmonary fitness, a template might emphasize high-intensity interval training and heart rate monitoring.

The instruction generation module then uses a natural language processing algorithm to analyze and match the input data to determine the most appropriate template. The algorithm can populate and adjust variables within the template based on a user's health data and training objectives. For example, specific values such as the user's age, weight, and heart rate can be substituted into the template to generate personalized natural language instructions.

In some embodiments, to improve the accuracy and practicality of the instruction, the instruction generation module can also integrate data validation and feedback mechanisms. After generating the instruction, the module checks whether the data in the instruction is logically consistent with medical common sense. For example, it checks whether the heart rate value is within a reasonable range and whether the exercise intensity recommendation is consistent with the user's health status. If any data anomalies or logical errors are detected, the instruction generation module automatically triggers a correction process and regenerates the instruction.

Natural language descriptions can integrate multi-dimensional information such as the target user's training objectives, health data, and static and dynamic physiological indicators into a semantically coherent and informative instruction. This representation not only captures the user's various features but also preserves the semantic details of the original data. For example, "A user wishes to train for a marathon, is 25 years old, weighs 60 kg, has mild knee discomfort, and has a current heart rate of 120 beats per minute" seamlessly integrates the user's training objective (marathon training), basic physical condition (age, weight), health concerns (knee discomfort), and real-time physiological status (heart rate). Compared to structured data tables, this natural language representation more naturally expresses complex, multi-dimensional related information, providing subsequent model processing with input that is more aligned with human cognitive habits and helps generate output that better meets the user's actual needs.

In some embodiments, operation S104 includes performing inference parsing on the natural language instruction using a pre-adapted target large language model to obtain user profile parsing information.

To achieve efficient inference and parsing, the target large language model undergoes a pre-adaptation (also known as fine-tuning) process. This pre-adaptation includes training with an extensive text data related to treadmill applications, encompassing various fitness scenarios, user health profiles, and exercise physiology knowledge. For example, text data containing descriptions of diverse user profiles, training objectives, and health conditions, as well as corresponding exercise recommendations and treadmill parameter settings, can be collected. By adapting this data, the target large language model learns how to map key information in the natural language instruction to specific user profiles, thereby providing an accurate foundation for subsequent parsing.

Subsequently, a multi-stage processing flow can be employed to improve the accuracy and comprehensiveness of the parsing of the natural language instruction. First, the target large language model performs preliminary semantic understanding and key information extraction on the input sentence, identifying entities (such as the user's age, weight, heart rate, etc.) and relationships (such as the relationship between training objectives and health conditions) within the sentence. Next, the target large language model leverages its internal attention mechanism to assign weights to different parts of the sentence, highlighting key information and reducing the weight of irrelevant or secondary content. For example, if a sentence mentions a user's history of heart disease and their current high-intensity training objectives, the target large language model may assign higher weight to the heart disease history because it significantly impacts the user's exercise safety. Through this multi-stage processing approach, the target large language model can more accurately parse user profiles, providing reliable support for generating personalized treadmill control strategies.

In addition, to further enhance the target large language model's inferencing performance, knowledge graph technology can be integrated. Knowledge graphs store entities, concepts, and their relationships in fields related to fitness and exercise physiology, such as appropriate exercise types for different health issues and the impact of various exercise parameters on fitness outcomes. As the target large language model parses natural language instructions, it can query the knowledge graph in real time to match and associate information in the sentence with entities and relationships within the knowledge graph. For example, if the target large language model determines that a user's goal is to improve cardiopulmonary function and that the user has mild asthma, the knowledge graph can be configured to retrieve aerobic exercise methods and precautions suitable for asthma patients and incorporate this information into the user profile analysis results. This not only enriches the content of the analysis information but also ensures the scientific and reasonable nature of the analysis results, providing a more comprehensive and accurate description of the user's features for subsequent decision-making agents.

The large language model has been extensively trained in natural language processing and possesses strong semantic understanding, contextual understanding, and text generation capabilities. It can deeply parse the key information in these natural language instructions, understand the user's true needs and physical condition, and transform this information into a structured user profile analysis. For example, for the user profile parsing information "a user desires marathon training, is 25 years old, weighs 60 kg, has mild knee discomfort, and has a current heart rate of 120 beats per minute," it can identify the need for long-term, high-intensity endurance training associated with "marathon training," and the potential risk of knee impact associated with "mild knee discomfort," which implies the need for appropriate exercise intensity control and reduced knee impact. Furthermore, the large language model can generate detailed, semantically logical user profiles based on the parsing results, providing a clear, accurate, and comprehensive basis for further decision-making, something that traditional data processing methods struggle to match.

Furthermore, a vast amount of knowledge in the sports and fitness field, including training methods, exercise physiology, and health advice, often exists in natural language form, such as in professional literature, fitness guides, and coaching advice. Therefore, by adaptively adjusting the large language model, this rich domain knowledge can be incorporated into model training. This allows the large language model to incorporate domain knowledge into inferencing and parsing when processing user data, generating more professional and scientific user profile information. For example, after learning insights such as "marathon training requires gradually increasing running distance to improve endurance" and "knee problems should avoid prolonged, high-intensity exercise," the model can better understand the relationship between user goals and physical conditions, providing more precise guidance to the decision-making agent and helping it develop more effective treadmill control strategies. According to some embodiments of the present disclosure, generating instructional language based on the training objective, user health data, static physiological data, and dynamic physiological data in operation S103 to obtain a natural language instruction may include the following operations.

Operation S201 includes obtaining key exercise instruction information for a target user by extracting key information from the training objective information, the user health data, the static physiological data, and the dynamic physiological data.

Operation S202 includes generating natural language based on the key exercise instruction information to obtain an intermediate instruction and perform sentence check on the intermediate instruction.

Operation S203 includes determining the intermediate instruction as a natural language instruction in response to the intermediate instruction passing the sentence check.

In some embodiments, operation S201 includes obtaining key exercise instruction information for a target user by extracting key information from the training objective information, the user health data, the static physiological data, and the dynamic physiological data.

According to the embodiments of the present disclosure, key information extraction from the collected user data is firstly required. This involves analyzing and filtering various user-entered information to determine which information is most critical for generating exercise instructions. For example, the static physiological data such as age, weight, height, and gender, as well as the dynamic physiological data such as heart rate and blood pressure, are important factors influencing exercises. The training objective information, according to the embodiments of the present disclosure, needs to be able to identify the user's specific goals, such as weight loss, muscle gain, and cardiopulmonary function improvement. The user health data includes medical history, chronic diseases, allergies, and other information, which is crucial for ensuring exercise safety. For example, for a 35-year-old user weighing 80 kg and 175 cm tall, whose training objective is weight loss and who has mild hypertension, according to the embodiments of the present disclosure, this key information is extracted to form key exercise instruction information. This information serves as the basis for generating exercise instructions.

In some embodiments, operation S202 includes generating natural language based on the key exercise instruction information to obtain an intermediate instruction and perform sentence check on the intermediate instruction.

In the embodiments of the present disclosure, after extracting the key information, a natural language generation model is utilized to convert this information into an intermediate instruction in natural language. This process requires consideration of language fluency, accuracy, and readability. In the embodiments of the present disclosure, the key information is embedded into an appropriate sentence structure based on preset sentence templates and grammatical rules. For example, based on the extracted key information, the intermediate instruction generated might be: "A 35-year-old male user, 175 cm tall, weighing 80 kg, aims to lose weight and has mild hypertension. Please generate a suitable treadmill training plan for him." After generating the sentence, sentence check is performed to ensure that the sentence contains no grammatical errors, is complete, and has clear logic. If errors or ambiguities are found in the sentence, corrections may be made until the sentence meets high-quality standards.

In some embodiments, operation S203 includes determining the intermediate instruction as a natural language instruction in response to the intermediate instruction passing the sentence check.

Once the intermediate instruction passes the sentence check, according to the embodiments of the present disclosure, it is determined as a natural language instruction. This operation completes the instruction generation process, and the natural language instruction may be used for subsequent large language model inference and parsing. The quality of natural language instruction is directly related to the accuracy and effectiveness of subsequent model inference and parsing. This method can be configured to improve the quality of natural language instruction before determining the instruction.

According to some embodiments of the present disclosure, before performing inference parsing on the natural language instruction using a pre-adapted target large language model to obtain user profile parsing information at operation S104, the method further includes pre-adapting the target large language model. The method may include the following operations.

Operation S301 includes obtaining sports domain knowledge data, training target sample data, user sample data, and an original natural language large model.

Operation S302 includes generating an instruction based on the sports domain knowledge data, the training target sample data, and the user sample data to obtain multiple instruction sample data.

Operation S303 includes performing annotation on each instruction sample data to obtain instruction annotation information corresponding to each instruction sample data.

Operation S304 includes constructing an adaptation dataset based on the multiple instruction sample data and the instruction annotation information corresponding to each instruction sample data.

Operation S305 includes performing adaptive training on the natural language model based on the adaptation dataset.

Operation S306 includes determining the natural language model as a target large language model in response to the natural language model satisfying a preset adjustment condition during the adaptive training.

In some embodiments, operation S301 includes obtaining sports domain knowledge data, training target sample data, user sample data, and an original natural language large model.

A large amount of knowledge data related to sports and fitness is collected. This data may include professional sports training methods, exercise physiology knowledge, strategies for achieving common fitness goals, and preventive measures for sports injuries. For example, professional literature and guidelines on how to improve cardiopulmonary function through treadmill training and how to conduct effective weight loss training may be collected. In addition, training objective sample data needs to be collected. This data covers common user fitness goals, such as weight loss, muscle building, and endurance improvement. User sample data includes basic information and exercise history of users of different ages, genders, and physical conditions. This data can be obtained from fitness apps, health surveys, and other sources. Furthermore, a large, original natural language model is required as a basis for adaptation.

In some embodiments, the sports domain knowledge data may include treadmill training plans, heart rate control methods, and exercise physiology principles. The training objective sample data may include goals such as weight loss, muscle building, and cardiopulmonary function improvement. The user sample data may include basic information such as the user's age, weight, health status (such as heart disease, knee problems, and other health issues), and exercise history.

In some embodiments, operation S302 includes generating an instruction based on the sports domain knowledge data, the training target sample data, and the user sample data to obtain multiple instruction sample data.

The instruction sample data is generated using the collected data. The instruction sample data are intended to simulate user needs and physical condition descriptions that may be encountered in actual usage scenarios. The instruction sample data needs to cover different user profiles, training objectives, and health conditions.

In some embodiments, the generated instruction sample data may include: "User A, 30 years old, weighs 80 kg, aims to lose weight, has mild knee pain, and desires low-intensity treadmill training," "User B, 45 years old, weighs 70 kg, aims to improve cardiopulmonary function, has a history of hypertension, and desires moderate-intensity treadmill training," and "User C, 25 years old, weighs 60 kg, aims to increase endurance, has no health issues, and desires high-intensity treadmill training."

In some embodiments, operation S303 includes performing annotation on each instruction sample data to obtaining instruction annotation information corresponding to each instruction sample data.

The annotation is intended to provide corresponding annotation information for each instruction sample data. The annotation information includes user profile analysis, training objective analysis, health status analysis, etc. The annotation information serves as a supervisory signal for model training, helping the model learn how to extract key information from natural language instructions.

In some embodiments, operation S304 includes constructing an adaptation dataset based on the multiple instruction sample data and the instruction annotation information corresponding to each instruction sample data.

The adaptation dataset includes the adaptive instructional sample data and the corresponding annotation information. The adaptation dataset may be configured to train a large natural language model to adapt it to the specific needs of the sports and fitness field. The construction of the adaptation dataset requires ensuring sample diversity and representativeness to cover a variety of user profiles, training objectives, and health conditions.

In some embodiments, operation S305 includes performing adaptive training on the natural language model based on the adaptation dataset.

In the present operation, the constructed adaptation dataset is configured to adaptively train the original natural language model. The goal of adaptive training is to enable the natural language model to accurately extract user profile parsing information from the natural language instruction. During the training process, the natural language model learns how to map key information in the instruction to the structured data in the annotation information.

According to some embodiments of the present disclosure, operation 305 which includes performing adaptive training on the natural language model based on the adaptation dataset, may include the following operations: selecting instruction sample data from the adaptation dataset and inputting the instruction sample data into the natural language model to obtain a current round of adaptive training output; querying instruction annotation information corresponding to the instruction sample data from the adaptation dataset, and performing difference analysis on the instruction annotation information and the current round of adaptive training output to obtain the current round of deviation data; performing model adaptation on the natural language model based on the current round of deviation data to update the natural language model; returning to execute selecting instruction sample data from the adaptation dataset to input into the natural language model until the current round of deviation data is less than a preset expected value based on the updated natural language model to determine that the natural language model meets an expected adjustment condition during the adaptive training.

In some embodiments of the present disclosure, the process of adaptively training the natural language model based on the adaptation dataset is an iterative optimization process designed to enable the natural language model to accurately extract user profile parsing information from the natural language instruction.

At the beginning of the training process, a batch of instruction sample data is selected from the adaptation dataset as an input to the natural language model. The sample data are carefully designed and prepared to cover diverse user profiles, training objectives, and health conditions. The natural language model processes these input sentences based on the current parameter settings and generates corresponding output results, known as the adapted output results for this round. This output represents the natural language model's understanding and parsing of the input instructions in its current training state.

After obtaining the natural language model output results, they need to be compared with the corresponding instruction annotation information in the adapted dataset. The instruction annotation information can be pre-generated by experts in the field of sports and fitness or through other reliable methods, providing standard answers and containing all the key information to be extracted from the instructions. By comparing the natural language model output and the annotation information, the difference between the two can be calculated, known as the deviation data for this round. This deviation data quantifies the difference between the natural language model's current output and the expected output. For example, if the natural language model's output for the above instruction sample data omits the health condition information "mild knee pain," this omission may be identified when compared with the annotation information and reflected in the deviation data.

Based on the deviation data obtained in this round, an optimization algorithm (such as gradient descent) is configured to adjust the parameters of the large natural language model. The goal is to reduce the discrepancy between the output of the large natural language model and the annotation information, enabling the large natural language model to more accurately parse instructional sentences in the next round of training. This process involves a large number of parameter updates and calculations within the large natural language model, aiming to gradually improve its performance.

It's important to emphasize that adaptive training is an iterative process. After a parameter update, the natural language model may again select indicator sample data from the adaptation dataset for processing, repeating the aforementioned operations. Each iteration calculates new deviation data and uses this data to further adjust the natural language model parameters. This cycle continues until the deviation data falls below a preset expected value, meaning that the difference between the natural language model's output and the annotation information is sufficiently small to meet the expected training conditions.

For example, after multiple rounds of iterative training, when the natural language model accurately captures all key information in the majority of indicator sample data and the deviation data reaches a preset lower threshold, the natural language model can be considered to have completed adaptive training and can accurately interpret user profile information, providing reliable support for subsequent treadmill control strategy generation.

Through the above process, how systematic adaptive training of the natural language model enables it to accurately understand and interpret user profile information, is demonstrated, laying the foundation for the development of personalized treadmill training plans.

In some embodiments, operation S306 includes determining the natural language model as a target large language model in response to the natural language model satisfying a preset adjustment condition during the adaptive training.

During model training, certain adaptation conditions need to be set, such as the natural language model's accuracy on the validation set reaching a certain threshold, or the loss function reaching a certain level. When the natural language model satisfies these conditions during training, it is determined as the target large language model. The target large language model may be used for subsequent inferencing and parsing to generate user profile parsing information.

In some embodiments, assume that the preset condition is that the model's accuracy on the validation set reaches above 90%. When the model reaches 92% accuracy on the validation set after multiple rounds of training, the model is deemed to meet the expected conditions and can be determined as the target large language model.

In this way, according to some embodiments of the present disclosure, the professionalism and accuracy of the target large language model in processing information in the field of sports and fitness is ensured, providing a reliable foundation for the subsequent generation of personalized treadmill control strategies.

In some embodiments, operation S105 includes generating, by a pre-trained decision-making agent, a treadmill control policy adapted to the target user based on the user profile parsing information.

During the pre-training process, the decision-making agent may utilize training data encompassing diverse user profiles and corresponding treadmill control strategies. This data can be obtained from historical treadmill usage records, including the user's static and dynamic physiological indicators, training objectives, and corresponding treadmill settings. To improve data quality and practicality, data cleaning and preprocessing techniques can be applied to remove outliers and noise, and the data is normalized to ensure consistent multi-dimensional analysis.

In some embodiments, the decision-making agent can process multi-dimensional user profile parsing information and comprehensively consider the impact of various factors on treadmill control. For example, when the analysis information includes data such as the user's maximum heart rate, target heart rate range, and joint flexibility, the decision-making agent can extract key information through feature engineering and utilize a multi-objective optimization algorithm to weigh the relationships between different factors. For an elderly user who wants to improve cardiopulmonary function but also has joint issues, the intelligent agent may need to increase heart rate while limiting incline to protect joints. This can be achieved by constructing a decision-making model that considers multiple objective functions, such as minimizing heart rate deviation and maximizing comfort, while ensuring a certain level of exercise intensity.

In some embodiments, to ensure real-time and adaptable strategies, the decision-making agent needs to possess online learning and dynamic adjustment capabilities. During actual operation, the decision-making agent can also allocate a data reception channel to directly and continuously receive the user's real-time dynamic physiological data and adjust the treadmill's operating state in real time based on this data. For example, if the user's real-time heart rate exceeds the target range, the decision-making agent should immediately implement a pre-set emergency strategy, such as reducing the speed or pausing the treadmill, and promptly send a reminder to the user. Furthermore, the decision-making agent can dynamically adjust its internal model parameters based on the user's long-term exercise data and feedback to adapt to changes in the user's physical condition and athletic ability. This can be achieved by implementing an incremental learning algorithm or periodically retraining the model to ensure that the intelligent agent's strategy always matches the user's latest needs and physical condition.

Through this implementation, the pre-trained decision-making agent can generate accurate, safe, and efficient treadmill control strategies based on a thorough understanding of the user's features, meeting the user's personalized fitness needs and enhancing the treadmill's intelligence and user experience. The combination of a large language model and a decision-making agent represents a deep fusion, fully leveraging the strengths of both in natural language processing and decision control. This combination demonstrates excellent performance in processing complex user data, leveraging domain knowledge, providing personalized services, and continuously optimizing system performance.

According to some embodiments of the present disclosure, operation S105 includes generating, by a pre-trained decision-making agent, a treadmill control policy adapted to the target user based on the user profile parsing information. Operation S105 may include the following operations.

Operation S401 includes retrieving, by a decision-making agent, knowledge entity information associated with the user profile parsing information from a pre-built knowledge graph database.

Operation S402 includes integrating the user profile parsing information with the knowledge entity information to obtain contextual exercise representation information corresponding to the target user.

Operation S403 includes generating a control strategy based on the contextual exercise representation information to obtain a treadmill control strategy adapted for the target user.

In some embodiments, operation S401 includes retrieving, by a decision-making agent, knowledge entity information associated with the user profile parsing information from a pre-built knowledge graph database.

First, the decision-making agent has access to a pre-built knowledge graph database containing a wealth of knowledge in the field of sports and fitness. The knowledge entity information in the knowledge graph covers various sports-related concepts and their interrelationships, such as different training objectives (e.g., weight loss, muscle gain), health conditions (e.g., high blood pressure, joint problems), exercise types (e.g., treadmill training, strength training), exercise parameters (e.g., speed, incline), and exercise recommendations tailored for different user profiles. After receiving the user profile parsing information, the decision-making agent retrieves knowledge entities associated with these features from the knowledge graph. For example, if the user's profile information indicates that the user's goal is weight loss and the user experiences mild knee pain, the decision-making agent may search the knowledge graph for knowledge entities related to "weight loss training" and "knee protection," such as low-impact treadmill training methods suitable for weight loss and exercise parameter settings that promote knee protection.

In some embodiments, operation S402 includes integrating user profile parsing information with knowledge entity information to obtain contextual exercise representation information corresponding to the target user.

After obtaining the knowledge entity information related to the user's profile, the decision-making agent fuses this information with the user's profile information. The purpose of this fusion process is to integrate the user's specific features with the general knowledge in the knowledge graph to form a comprehensive and personalized contextual exercise representation information. The representation information not only includes basic information such as the user's age, weight, and health status, but also incorporates professional exercise recommendations tailored to these features, such as appropriate exercise intensity, duration, and frequency. For example, for a user with a weight loss goal and knee pain, the fused contextual exercise representation information may include: the user's basic physical data, the calorie consumption target for weight loss, the appropriate low-impact running speed and incline range for the user, and the recommended duration of each training session. The representation information provides comprehensive contextual support for the subsequent generation of precise treadmill control strategies.

In some embodiments, operation S403 includes generating a control strategy based on the contextual exercise representation information to obtain a treadmill control strategy adapted for the target user.

The decision-making agent, based on the contextual exercise representation information, utilizes its internal decision-making algorithm to generate a treadmill control strategy tailored to the target user. The decision-making agent's algorithm may be based on reinforcement learning, deep learning, or other advanced machine learning techniques. These algorithms can consider multiple objective functions and constraint conditions, such as maximizing exercise effectiveness, ensuring exercise safety, and improving exercise comfort. When generating the control strategy, the algorithm determines the specific treadmill parameter settings based on the contextual exercise representation information. For example, for the user mentioned above, the decision-making agent might generate a treadmill control strategy with an initial speed of 4-5 km/h and an incline of 0%-3%, and recommend a training of 30-45 minutes per session, with 3-4 training sessions per week. Furthermore, the intelligent agent dynamically adjusts the strategy based on the user's real-time dynamic physiological indicators (such as heart rate and gait) to ensure a safe and effective training experience throughout the entire exercise process.

Through this process, the decision-making agent can fully leverage the professional sports knowledge in the knowledge graph and, in combination with the user's specific features, generate precise and personalized treadmill control strategies, thereby helping users achieve their fitness goals more scientifically.

According to some embodiments of the present disclosure, before generating, by a pre-trained decision-making agent, a treadmill control policy adapted to the target user based on the user profile parsing information at operation S105, the decision-making agent is also pre-trained. The method may specifically include the following operations.

Operation S501 includes constructing an exercise simulation process that matches multiple candidate users, the exercise simulation process configured to simulate a treadmill operation environment and the candidate users' exercise processes.

Operation S502 includes obtaining multiple user profile sample data and an original agent network.

Operation S503 includes processing, by an intelligent agent network, the user profile sample data to obtain a current round of training simulation strategy.

Operation S504 includes performing interactive simulation during the exercise simulation process using the current round of training simulation strategy to determine treadmill state simulation data and user state simulation data during the exercise simulation process.

Operation S505 includes calculating a simulation reward signal based on the treadmill state simulation data and the user state simulation data.

Operation S506 includes updating the intelligent agent network based on the simulation reward signal.

Operation S507 includes returning to process user profile sample data using the intelligent agent network based on the updated intelligent agent network until the current round of training simulation strategy meets a preset training expectation, and generating a decision-making agent based on the intelligent agent network.

Operation S501 includes constructing an exercise simulation process that matches multiple candidate users, the exercise simulation process configured to simulate a treadmill operation environment and the candidate users' exercise processes.

Constructing an environment that can simulate treadmill operation and user exercise processes is the basis for training the decision-making agent. The exercise simulation process is able to simulate the responses of different types of users and various treadmill operating states. For example, treadmill training at different speeds and inclines can be simulated for users of different ages, weights, and health conditions, including their heart rate variability, fatigue levels, and movement trajectories. The simulation environment provides a safe and controllable training platform for the intelligent agent, enabling it to accumulate extensive experience in a virtual environment without the need for actual hardware testing.

In some embodiments, operation S502 includes obtaining multiple user profile sample data and an original agent network.

The multiple user profile sample data collected includes information such as the user's age, weight, height, gender, health status, and training objectives. In addition, the original agent network, which can be a deep neural network, is obtained as the initial model for the decision-making agent. For example, profile sample data can be collected for 1,000 different users, ranging from young to elderly, and from healthy individuals to those with minor health issues.

In some embodiments, operation S503 includes processing, by an intelligent agent network, the user profile sample data to obtain a current round of training simulation strategy.

The intelligent agent network processes the user profile sample data and generates a current training simulation strategy. The current training simulation strategy defines how the intelligent agent network adjusts treadmill parameters based on the user's features within the simulation environment. For example, for a young, healthy user, the current training simulation strategy might recommend a higher speed and incline, whereas for an older user, the current training simulation strategy might recommend a lower speed and incline to ensure safety.

In some embodiments, operation S504 includes performing interactive simulation during the exercise simulation process using the current round of training simulation strategy to determine treadmill state simulation data and user state simulation data during the exercise simulation process.

Within the simulation environment, the intelligent agent interacts with the environment based on the generated simulation strategy. In this way, the treadmill state simulation data (such as speed, incline, time, etc.) and the user state simulation data (such as heart rate, gait, fatigue level, etc.) can be collected. This data reflects the actual effectiveness of the intelligent agent strategy within the simulation environment. For example, during an exercise simulation, the intelligent agent network may try different speed and incline combinations to observe the simulated user's heart rate response and exercise performance.

In some embodiments, operation S505 includes calculating a simulation reward signal based on the treadmill state simulation data and the user state simulation data.

The simulated reward signal is calculated based on the collected treadmill state simulation data and the user state simulation data. This reward signal is configured to evaluate the effectiveness of the intelligent agent strategy and can be based on the user's exercise effectiveness (such as calorie consumption and cardiopulmonary function improvement) and safety (such as avoiding overexertion or injury). For example, if the user achieves the expected exercise intensity in the simulation and does not experience abnormal physical reactions, the intelligent agent network may receive a high reward signal.

In some embodiments, operation S506 includes updating the intelligent agent network based on the simulation reward signal.

The intelligent agent network is updated based on the simulated reward signal, and a reinforcement learning algorithm may be used. This process adjusts the parameters of the intelligent agent network to strengthen strategies that achieve high rewards and weaken strategies that result in low rewards. For example, if a strategy causes the user's heart rate to be too high, the intelligent agent may reduce the weight of that strategy; conversely, if a strategy effectively helps the user achieve their exercise goals, the intelligent agent may increase the weight of that strategy.

In some embodiments, operation S507 includes returning to process user profile sample data using the intelligent agent network based on the updated intelligent agent network until the current round of training simulation strategy meets a preset training expectation, and generating a decision-making agent based on the intelligent agent network.

The training process is iterative, with the intelligent agent network continuously updated and optimized. After each update, the intelligent agent network processes the user profile sample data again and tests it in the simulation environment. This cycle continues until the intelligent agent network's strategy meets a preset training expectation, such as reaching a certain reward threshold or achieving strategy stability. Once the condition is met, the training process ends, and the resulting agent network is determined to be the decision-making agent, ready for use in actual treadmill control.

Through this pre-training process, the decision-making agent can generate accurate and safe treadmill control strategies based on user profile parsing information in real-world applications, helping users effectively achieve their fitness goals.

According to some embodiments of the present disclosure, operation S104 which includes performing inference parsing on the natural language instruction using a pre-adapted target large language model to obtain user profile parsing information, may include the following operations: uploading the natural language instruction to a target large language model deployed on a cloud server; and obtaining the user profile parsing information by performs inference and parsing on the natural language instruction by the target large language model.

Operation S105 which includes generating, by a pre-trained decision-making agent, a treadmill control policy adapted to the target user based on the user profile parsing information, may include the following operations: generating, by the decision-making agent deployed on the cloud server, a treadmill control policy adapted for the target user based on the user profile parsing information.

Uploading the natural language instruction to the target large language model on the cloud server ensures that the model receives a complete sentence that includes the user's training objectives, health data, and physiological indicators. The cloud server provides powerful computing power and storage resources, enabling efficient operation and data processing of large-scale models. After receiving the instruction, the target large language model leverages its expertise in the sports and fitness field and its natural language processing capabilities to perform in-depth semantic analysis and feature extraction on the sentence.

Further, the decision-making agent on the cloud server generates an adapted treadmill control policy based on the user profile parsing information. The decision-making agent runs on the cloud server and can access and process a large amount of user data and expertise in the sports and fitness field.

The deployment of cloud servers not only provides powerful computing support but also ensures data security and privacy. User data is encrypted during transmission and processing to prevent data leakage and unauthorized access. Furthermore, the cloud servers can update and optimize models in real time, ensuring that the decision-making agent and large language model always make decisions based on the latest sports and fitness knowledge and user feedback, thereby providing users with more accurate and personalized services. Through the above process, how to leverage the powerful computing power of cloud servers and intelligent model processing to achieve efficient conversion from natural language instructions to personalized treadmill control strategies is demonstrated, helping users better achieve their fitness goals.

According to some embodiments of the present disclosure, operation S104 which includes performing inference parsing on the natural language instruction using a pre-adapted target large language model to obtain user profile parsing information, may include the following operation: uploading the natural language instruction to the target large language model deployed on the terminal device, and inferring and parsing the natural language instruction using the target large language model to obtain user profile parsing information.

Operation S105 which includes generating, by a pre-trained decision-making agent, a treadmill control policy adapted to the target user based on the user profile parsing information, may include the following operation: generating, by a decision-making agent deployed on a terminal device, a treadmill control policy adapted for the target user based on the user profile parsing information.

In the embodiments, the processing of the natural language instruction is performed on the terminal device, which reduces reliance on network connectivity and improves the real-time nature and privacy of data processing. The target large language model is optimized and compressed to run efficiently within the limitations of the hardware of the terminal device. For example, through model quantization and pruning techniques, the model size and computational requirements are significantly reduced, enabling it to run on a smartphone or dedicated fitness device. This local processing approach not only speeds up response time but also ensures that the user's health data does not leave the device, thereby enhancing data security.

Furthermore, based on the user profile parsing information, the decision-making agent deployed on the terminal device can generate an adaptive treadmill control strategy in real time. The implementation of the decision-making agent on the terminal device has also been optimized to ensure efficient operation in resource-constrained environments. It leverages the device's local computing power and combines the user's real-time dynamic physiological data (such as heart rate and gait, which may be derived from a connected smart wearable device) to quickly develop a personalized exercise plan.

The advantage of performing these operations on the terminal device is that it provides a more personalized and immediate user experience. Users can receive real-time exercise guidance and treadmill setting recommendations without having to wait for a response from a cloud server. Furthermore, this localized processing approach reduces data transmission costs and mitigates security risks associated with network latency. In summary, by deploying the target large language model and the decision-making agent on the terminal device, fast, secure, and efficient personalized treadmill control is achieved, providing users with a more intelligent fitness solution.

According to some embodiments of the present disclosure, operation S104 which includes performing inference parsing on the natural language instruction using a pre-adapted target large language model to obtain user profile parsing information, may include the following operation: uploading the natural language instruction to the target large language model deployed on the treadmill and parsing the natural language instruction using the target large language model to obtain the user profile parsing information.

Operation S105 which includes generating, by a pre-trained decision-making agent, a treadmill control policy adapted to the target user based on the user profile parsing information, may include the following operation: generating, by a decision-making agent deployed on the treadmill, a treadmill control policy tailored to the target user based on the user profile parsing information.

The target large language model can also be built into the treadmill. This target large language model has been optimized and adapted specifically for the sports and fitness field. The user can directly enter a natural language instruction on the treadmill interface. Upon receiving this instruction, the large language model on the treadmill immediately performs semantic analysis and feature extraction. Leveraging its expertise in the sports and fitness field, the model accurately parses key information such as the user's age, gender, weight, training objectives, and health status to generate user profile parsing information. This localized processing approach not only speeds up data processing but also enhances user data privacy, as data is processed directly within the treadmill without being uploaded to the cloud.

Furthermore, the treadmill also incorporates a pre-trained decision-making agent that can generate personalized treadmill control policies in real time based on the user profile parsing information. Deploying the decision-making agent on the treadmill ensures it can quickly respond to user needs and dynamically adjust based on the user's real-time dynamic physiological data (such as heart rate and gait, which may be derived from the treadmill's built-in sensors).

Deploying the target large language model and the decision-making agent directly on the treadmill enables the entire system to operate independently, without relying on an external network connection. This design not only improves reliability and response speed but also reduces network latency and data transmission costs. Users can use the treadmill anytime, anywhere, and receive instant personalized exercise guidance and control strategies. In summary, by directly deploying the target large language model and decision-making agent on the treadmill, fast, safe, and efficient personalized treadmill control may be achieved, providing users with a more intelligent fitness solution.

In some embodiments, operation S106 includes controlling an operating state of the treadmill based on the treadmill control policy.

In embodiments of the present disclosure, the treadmill's hardware system and the decision-making agent have an efficient communication mechanism, enabling the treadmill to receive control signals from the intelligent agent and convert them into specific hardware operation instructions. For example, the speed adjustment signal sent by the decision-making agent based on the treadmill's control strategy is received by the treadmill's microcontroller, which in turn controls the treadmill's motor drive module to achieve precise speed regulation.

In some embodiments, a closed-loop control system can be added to achieve precise treadmill operating state control. The closed-loop control system uses various sensors installed on the treadmill, such as speed sensors and incline sensors, to monitor the treadmill's actual operating state in real time and feed this data back to the decision-making agent. The intelligent agent compares this feedback data with the treadmill's control strategy, calculates a deviation, and adjusts the control signal accordingly to minimize the deviation. For example, if the target speed is 10 km/h and the actual speed is 9.8 km/h, the decision-making agent calculates a corresponding compensation signal based on the deviation, increasing the motor drive current to increase the speed until the actual speed matches the target speed. This closed-loop control approach effectively addresses performance fluctuations caused by factors such as load changes and mechanical wear during treadmill operation, ensuring that the treadmill always operates stably according to the intended control strategy.

In some embodiments, the treadmill also incorporates an intelligent shock absorption system that automatically adjusts the hardness of the treadmill's shock-absorbing pad based on the user's weight and exercise intensity, providing a more comfortable exercise environment.

According to the embodiments of the present disclosure, a smart collaborative approach is achieved, forming a closed-loop control system encompassing data collection, semantic transformation, model analysis, strategy generation, and device control. During operation, the smart wearable device collects the user's dynamic physiological data in real time and feeds it back to the control system, where it is integrated with the user's profile parsing information. The decision-making agent adjusts the treadmill's control strategy in real time based on the updated user state information, and precisely executes the corresponding operating state changes through the treadmill's hardware control system. For example, if the user's real-time heart rate indicates that it is approaching a preset safety threshold for the user's maximum heart rate, the intelligent agent quickly responds by reducing the treadmill's speed or incline to ensure that the user's heart rate returns to a safe range. Furthermore, the treadmill's display or voice system can provide users with timely feedback on current adjustments and subsequent training suggestions, enhancing their sense of control and engagement in the training process and improving overall exercise experience.

According to some embodiments of the present disclosure, after operation S106 which includes controlling an operating state of the treadmill based on the treadmill control policy, the following operations may also be included.

Operation S601 includes recollecting, by a smart wearable device, the dynamic physiological data of the target user.

Operation S602 includes based on the recollected dynamic physiological data, generating an instruction based on the training objective information, the user health data, the static physiological data, and the dynamic physiological data to continuously update the treadmill control policy.

In some embodiments of the present disclosure, the process of recollecting the dynamic physiological data and continuously updating the treadmill control policy by the smart wearable device after operation S106 forms a closed-loop feedback mechanism, ensuring that the user consistently receives the most optimized training experience throughout their exercise.

In some embodiments, operation S601 includes recollecting, by a smart wearable device, the dynamic physiological data of the target user.

During treadmill operation, the user's smart wearable device (such as a smartwatch, heart rate monitor, etc.) continuously monitors the dynamic physiological data, including heart rate, blood pressure, gait, calorie consumption, etc. For example, a smartwatch can update heart rate data once per second, while a heart rate monitor can provide more accurate real-time heart rate monitoring. This dynamic data reflects the user's physical response and exercise status under the current treadmill settings and is a key indicator for evaluating training effectiveness and safety.

In some embodiments, operation S602 includes based on the recollected dynamic physiological data, returning to execute an instruction generation based on the training objective information, the user health data, the static physiological data, and the dynamic physiological data to continuously update the treadmill control policy.

After recollecting the dynamic physiological data, a natural language instruction can be regenerated by combining the original training objective, the user health data, the static physiological data, and the latest dynamic physiological data. This process is similar to the initial instruction generation operation, but this time it is based on existing exercise data and reflects real-time changes in the user's exercise status. For example, if the user's real-time heart rate is close to 85% of the user's maximum heart rate, and the current treadmill settings may be too high, a new instruction may be generated: "The user's current heart rate is high. Reduce the speed to 5 km/h and the incline to 2% to ensure safety." This instruction may trigger the target large language model to reparse user profiles, and the decision-making agent may adjust the treadmill's operating state.

According to some embodiments of the present disclosure, operation S602 which includes based on the recollected dynamic physiological data, returning to execute an instruction generation based on the training objective information, the user health data, the static physiological data, and the dynamic physiological data to continuously update the treadmill control policy, may further include the following operations.

Operation S701 includes based on the recollected dynamic physiological data, returning to execute an instruction generation based on the training objective information, the user health data, the static physiological data, and the dynamic physiological data to obtain an updated natural language instruction.

Operation S702 includes inferencing and parsing, by the target large language model, the updated natural language instruction to obtain updated user profile parsing information.

Operation S703 includes updating, by the decision-making agent, the treadmill control policy for the target user based on the updated user profile parsing information and a previous round of treadmill control policy.

Operation S704 includes controlling an operating state of the treadmill based on the updated treadmill control policy.

After recollecting the dynamic physiological data, the updated natural language instruction is re-input into the target large language model for inference and parsing. Based on the new instruction, the target large language model re-parses the user's profile information, including current exercise status and health status. For example, the target large language model might analyze that the user's heart rate is approaching 85% of their maximum heart rate, necessitating a reduction in exercise intensity to ensure safety. This analysis generates new user profile parsing information, such as: "The user's heart rate is high, and the current exercise intensity is too high. It is recommended to reduce the speed and incline."

Further, after receiving this updated user profile parsing information, the decision-making agent can combine it with the previous treadmill control policy to generate a new control policy. For example, the previous policy might be a speed of 6 km/h and an incline of 3%, while the new policy might be adjusted to a speed of 5 km/h and an incline of 2%. The intelligent agent comprehensively considers the user's training objectives, health status, and real-time dynamic physiological data to ensure that the new policy is both safe and effective. For example, for a user who wants to lose weight but has a high heart rate, the decision-making agent might further reduce the speed and incline while increasing the interval time to ensure that the user can continue training within a safe heart rate range.

Furthermore, the treadmill can adjust its operating state based on the updated control strategy. For example, the treadmill's speed might automatically adjust from 6 km/h to 5 km/h, and the incline from 3% to 2%. Simultaneously, the treadmill's display or voice system may provide feedback to the user regarding the adjustment and new training suggestions, such as, "Your heart rate is high. We've reduced the speed and incline. Please maintain your current state and continue training." This real-time feedback and adjustment mechanism ensures that users maintain optimal training status throughout their workouts, while also avoiding the risks of overexertion.

According to some embodiments of the present disclosure, operation S703 which includes updating, by the decision-making agent, the treadmill control policy for the target user based on the updated user profile parsing information and a previous treadmill control policy, may further include the following operations.

Operation S801 includes evaluating, by the intelligent agent, the target user's current exercise state based on the updated user profile parsing information.

Operation S802 includes calculating a current speed change and a current incline change based on the current exercise state, the updated user profile parsing information, and the previous round of treadmill control policy.

Operation S803, generating a fluent control policy and updating the treadmill control policy based on the current round of speed change and the current round of incline change.

In embodiments of the present disclosure, the decision-making agent first comprehensively evaluates the target user's current exercise state based on the updated user profile parsing information. This includes dynamic physiological indicators data such as the user's real-time heart rate, blood pressure, gait, speed, and incline, as well as static physiological indicators data such as the user's age, weight, and health status. For example, if a user's real-time heart rate is 130 beats per minute (bpm) and the maximum safe heart rate is 150 bpm, the intelligent agent may determine that the user is currently exercising at a moderate intensity. The intelligent agent also considers the user's training objectives, such as weight loss, muscle building, or improving cardiorespiratory fitness, as well as the user's health status, such as a history of heart disease or joint problems. For example, for a user who wants to lose weight and has mild knee pain, the intelligent agent may pay special attention to their heart rate and gait to ensure that the exercise intensity is moderate and does not place excessive stress on the knees.

After assessing the user's current exercise state, the decision-making agent combines the updated user profile parsing information with the treadmill control policy from the previous round to calculate the speed change and incline change for the current round. This operation requires the intelligent agent to comprehensively consider multiple factors, including the user's training objectives, health status, current exercise intensity, and the effectiveness of the previous round's policy. For example, if the user's heart rate is slightly above the target range, the intelligent agent may calculate a small speed reduction (e.g., −0.5 km/h) and a small incline reduction (e.g., −1%) to gently reduce the exercise intensity. Conversely, if the user's heart rate is below the target zone and they show no signs of fatigue, the intelligent agent might calculate an appropriate speed increase (e.g., +0.5 km/h) and an appropriate incline increase (e.g., +1%) to improve exercise effectiveness.

Finally, the decision-making agent generates a fluent control policy based on the calculated speed and incline changes to update the treadmill's operating state. The goal of the fluent control policy is to ensure that speed and incline changes are not too drastic, thereby avoiding discomfort or increasing the risk of injury. For example, if the speed change for this round is −0.5 km/h and the incline change is −1%, the intelligent agent may generate a gradual adjustment policy to fluently transition the speed and incline to the new settings over a specified period. The intelligent agent might set a transition time of 30 seconds, reducing the speed by 0.1 km/h and the incline by 0.2% every 5 seconds until the target speed and incline are reached. This fluent adjustment not only improves user comfort but also helps them better adapt to the new exercise intensity, thereby enhancing training effectiveness.

Through the above process, the decision-making agent can dynamically adjust the treadmill's speed and incline based on the user's real-time exercise status and profile information, ensuring that the user remains in optimal training condition throughout the entire exercise process. This dynamic adjustment mechanism not only improves the safety and effectiveness of training but also provides users with personalized exercise experience, helping them achieve their fitness goals more scientifically.

The closed-loop feedback mechanism ensures that the treadmill's control strategy can be dynamically adjusted based on the user's real-time physical condition. For example, during a training session, the user might initially set a speed of 6 km/h and an incline of 3%. As the session progresses, the user's heart rate gradually increases. When the heart rate reaches a preset safety limit, the smart wearable device transmits data to the treadmill, which then reassesses and generates a new control strategy, reducing the speed and incline to ensure user safety. Furthermore, the reasons for the adjustments may be explained to the user through the treadmill's display or voice system and follow-up training recommendations may be provided. This real-time feedback and adjustment mechanism not only improves training safety but also helps users achieve their fitness goals more scientifically and optimizes overall exercise results.

According to embodiments of the present disclosure, the treadmill is configured to be controlled by any of the treadmill control methods described in the embodiments of the present disclosure. The treadmill in the embodiments integrates a large language model and a decision-making agent, combined with real-time data monitoring and feedback mechanisms, to provide users with a personalized, intelligent, safe, and efficient exercise solution. It not only helps users conduct fitness training more scientifically, but also enhances the comfort and enjoyment of exercise, while promoting long-term health management and the achievement of exercise goals.

Figure 2:
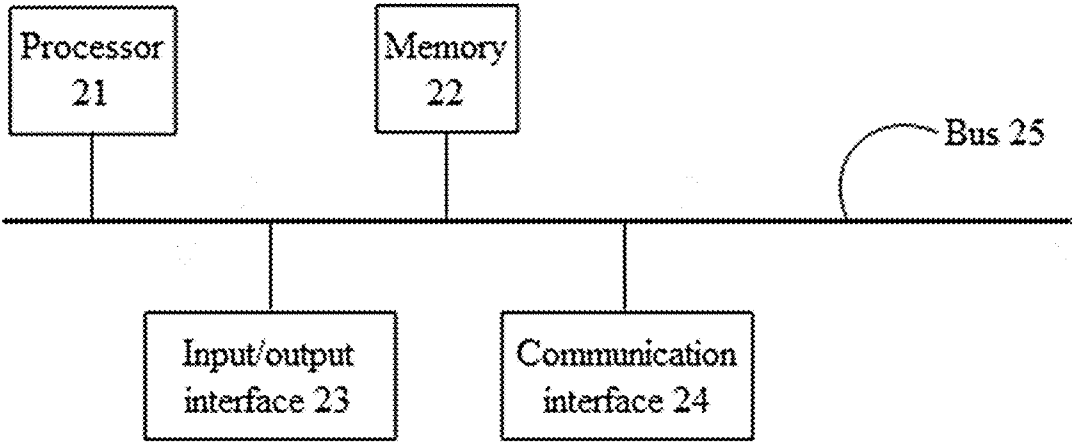
FIG. 2 is a schematic diagram of the hardware structure of an electronic device according to some embodiments of the present disclosure.

As illustrated in FIG. 2, which illustrates a hardware structure of an electronic device, in some embodiments, the electronic device may include a processor 21, a memory 22, an input/output interface 23, a communication interface 24, and a bus 25.

The processor 21, which may be implemented as a general-purpose CPU (Central Processing Unit), a microprocessor, an application-specific integrated circuit (ASIC), or one or more integrated circuits, is configured to execute relevant programs to implement the technical solutions provided in the embodiments.

The memory 22 may be implemented as a read-only memory (ROM), a static storage device, a dynamic storage device, or a random access memory (RAM). The memory 22 can store an operating system and other application programs. When implementing the technical solutions provided in the embodiments of the present disclosure through software or firmware, the relevant program code is stored in the memory 22 and is executed by the processor 21 to perform the treadmill control method of the embodiments of the present disclosure.

The input/output interface 23 is configured to input and output information.

The communication interface 24 is configured to enable communication between the present device and other devices. Communication can be achieved through wired methods (such as USB, network cables, etc.) or wireless methods (such as mobile networks, Wi-Fi, Bluetooth, etc.).

The bus 25 is configured to transmit information between the various components of the device (such as the processor 21, the memory 22, the input/output interface 23, and the communication interface 24).

The processor 21, the memory 22, the input/output interface 23, and the communication interface 24 communicate with each other within the device via the bus 25.

The present disclosure also provides a computer program product, which includes a computer program. A processor of a computer device reads and executes the computer program, enabling the computer device to implement the above-mentioned treadmill control method.

The treadmill control method according to the embodiment of the present application, when applied to control the treadmill, at least has the following beneficial effects.

The treadmill is configured with a wearable device, and the method first obtains the training objective information, user health data, and static physiological data of the target user. The dynamic physiological data of the target user is collected through the wearable device. Based on the training objective information, the user health data, the static physiological data, and the dynamic physiological data, natural language instructions are generated. The target large language model, after pre-adaptation adjustments, parses and infers the natural language instructions to obtain user profile parsing information. A pre-trained decision-making agent generates a treadmill adjustment strategy tailored to the target user based on the user profile parsing information. The treadmill's operational state is then controlled according to the adjustment strategy, thereby providing personalized operation methods for different users.

The additional aspects and advantages of the present disclosure is partially given in the description, partially become apparent from the description, or be learned through the practice of the present application.

The terms "first," "fourth," and so forth (if any) in the present disclosure and accompanying drawings are configured to distinguish similar items and are not necessarily configured to describe a particular order or sequential sequence. The terms used in this manner are interchangeable where appropriate, such that the embodiments of the present disclosure described herein can, for example, be implemented in an order other than that illustrated or described herein. Furthermore, the terms "includes" and "comprises," and any variations thereof, are intended to cover non-exclusive inclusions. For example, a process, method, system, product, or apparatus comprising a series of operations or elements is not necessarily limited to those operations or elements expressly listed but may include other operations or elements not expressly listed or inherent to such process, method, product, or apparatus.

In the present disclosure, "at least one (item)" means one or more, and "a plurality" means two or more. "And/or" is configured to describe an associative relationship between associated items, indicating that three relationships may exist. For example, "A and/or B" may mean only A exists, B alone, and A and B simultaneously. A and B can be singular or plural. The character "/" generally indicates an "or" relationship between the contextual associated items. "At least one of the following" or similar expressions refers to any combination of these items, including any combination of single or plural items. For example, at least one of a, b, or c can mean: a, b, c; "a and b"; "a and c"; "b and c"; or "a and b and c", where a, b, and c can be single or plural.

The technical solution of the present disclosure, or the portion that contributes to the related art, or all or part of the technical solution, can be embodied in the form of a software product. This computer software product is stored in a storage medium and includes instructions for enabling a computer device (such as a personal computer, a server, or a network device) to perform all or part of the operations of the various embodiments of the present disclosure. The aforementioned storage medium may include: a USB flash drive, a mobile hard drive, a read-only memory (ROM), a random-access memory (RAM), or a magnetic disk, or an optical disk, and other media capable of storing program code.

It should also be understood that the various implementations provided in the embodiments of the present disclosure may be arbitrarily combined to achieve different technical effects.

The above is a detailed description of some implementations of the present disclosure, but the present disclosure is not limited to the aforementioned implementations. A person skilled in the art may make various equivalent modifications or substitutions without departing from the spirit of the present disclosure, and such equivalent modifications or substitutions are encompassed within the scope of the claims of the present disclosure.

What is claimed is:

1. A treadmill control method configured to control a treadmill equipped with a smart wearable device, the method comprising:
 obtaining training objective information, user health data, and static physiological data of a target user;
 collecting, by the smart wearable device, dynamic physiological data of the target user;
 generating instructional language based on the training objective information, the user health data, the static physiological data, and the dynamic physiological data to obtain a natural language instruction;
 performing, by a pre-adapted target large language model, inferencing and parsing of the natural language instruction to obtain user profile parsing information;
 generating, by a pre-trained decision-making agent, a treadmill control policy adapted to the target user based on the user profile parsing information; and
 controlling an operating state of the treadmill based on the treadmill control policy.

2. The method according to claim 1, wherein before performing, by a pre-adapted target large language model, inferencing and parsing of the natural language instruction to obtain the user profile parsing information further includes pre-adapting the target large language model, the pre-adapting the target large language model comprises:
 obtaining sports domain knowledge data, training target sample data, user sample data, and an original natural language large model;
 generating an instruction based on the sports domain knowledge data, the training target sample data, and the user sample data to obtain a plurality of instruction sample data;
 annotating each of the plurality of instruction sample data to obtain instruction annotation information corresponding to each of the plurality of the instruction sample data;
 constructing an adapted dataset based on the plurality of instruction sample data and the instruction annotation information corresponding to each of the plurality of instruction sample data;
 performing adaptive training on the natural language large model based on the adapted dataset; and
 determining the natural language large model as a target large language model in response to the natural language large model satisfying a preset adjustment condition during the adapted training.

3. The method according to claim 1, wherein, before the generating, by the pre-trained decision-making agent, the treadmill control policy adapted to the target user based on the user profile parsing information; the method further comprises pre-training the decision-making agent, the pre-training the decision-making agent comprises:
 constructing an exercise simulation process matching multiple candidate users; wherein the exercise simulation process is configured to simulate a treadmill operation environment and the candidate users' exercise processes;
 obtaining multiple user profile sample data and an original agent network;
 processing, by an intelligent agent network, the user profile sample data to obtain a current round of training simulation strategy;
 performing interactive simulation during the exercise simulation process using the current round of training simulation strategy to determine treadmill state simulation data and user state simulation data during the exercise simulation process;
 calculating a simulation reward signal based on the treadmill state simulation data and the user state simulation data;
 updating the intelligent agent network based on the simulation reward signal; and
 returning to process user profile sample data using the intelligent agent network based on the updated intelligent agent network until the current round of training simulation strategy meets a preset training expectation, and generating a decision-making agent based on the intelligent agent network.

4. The method according to claim 1, wherein the generating, by the pre-trained decision-making agent, the treadmill control policy adapted to the target user based on the user profile parsing information comprises:
 retrieving, by a decision-making agent, knowledge entity information associated with the user profile parsing information from a pre-built knowledge graph database;
 integrating the user profile parsing information with the knowledge entity information to obtain contextual exercise representation information corresponding to the target user; and
 generating a control strategy based on the contextual exercise representation information to obtain a treadmill control strategy adapted for the target user.

5. The method according to claim 1, wherein after controlling the operating state of the treadmill based on the treadmill control strategy, the method further comprises:
 recollecting, by a smart wearable device, the dynamic physiological data of the target user; and
 based on the recollected dynamic physiological data, returning to generate an instruction based on the training objective information, the user health data, the static physiological data, and the dynamic physiological data to continuously update the treadmill control policy.

6. The method according to claim 5, wherein the based on the recollected dynamic physiological data, returning to execute the instruction generation based on the training objective information, the user health data, the static physiological data, and the dynamic physiological data to continuously update the treadmill control policy comprises:
 based on the recollected dynamic physiological data, returning to execute the instruction generation based on the training objective information, the user health data, the static physiological data, and the dynamic physiological data to obtain an updated natural language instruction;
 inferencing and parsing, by the target large language model, the updated natural language instruction to obtain updated user profile parsing information;
 updating, by the decision-making agent, the treadmill control strategy for the target user based on the updated user profile parsing information and a previous round of treadmill control strategy; and
 controlling the operating state of the treadmill based on the updated treadmill control strategy.

7. The method according to claim 6, wherein the updating, by the decision-making agent, the treadmill control strategy for the target user based on the updated user profile parsing information and the previous round of treadmill control strategy comprises:

evaluating, by the decision-making agent, a current exercise state of the target user based on the updated user profile parsing information;

calculating a current round of speed change and a current round of incline change based on the current exercise state, the updated user profile parsing information, and the previous round of treadmill control strategy;

generating a fluent control policy and updating the treadmill control policy based on the current round of speed change and the current round of incline change.

8. The method according to claim 1, wherein the collecting, by the smart wearable device, the dynamic physiological data of the target user, comprises the following:

collecting, by the smart wearable device, the physiological data from the target user once every sampling interval to update the dynamic physiological data.

9. The method according to claim 1, wherein the collecting, by the smart wearable device, the dynamic physiological data of the target user, comprises the following:

performing, by the smart wearable device, a physiological data monitoring operation on the target user to determine real-time monitored physiological data;

collecting the real-time monitored physiological data in response to the real-time monitored physiological data meeting a preset threshold setting condition; and updating the dynamic physiological data of the target user based on the real-time monitored physiological data.

10. The method according to claim 1, wherein the generating instructional language based on the training objective information, the user health data, the static physiological data, and the dynamic physiological data to obtain the natural language instruction comprises the following:

extracting key information from the training objective information, the user health data, the static physiological data, and the dynamic physiological data to obtain key exercise instruction information for the target user;

generating natural language based on the key exercise instruction information to obtain an intermediate instruction and perform sentence check on the intermediate instruction; and determining the intermediate instruction as a natural language instruction in response to the intermediate instruction passing the sentence check.

11. A treadmill configured to be controlled by a treadmill control method, the treadmill control method configured to control a treadmill equipped with a smart wearable device, the treadmill control method comprising:

obtaining training objective information, user health data, and static physiological data of a target user;

collecting, by the smart wearable device, dynamic physiological data of the target user;

generating instructional language based on the training objective information, the user health data, the static physiological data, and the dynamic physiological data to obtain a natural language instruction;

performing, by a pre-adapted target large language model, inferencing and parsing of the natural language instruction to obtain user profile parsing information;

generating, by a pre-trained decision-making agent, a treadmill control policy adapted to the target user based on the user profile parsing information; and controlling an operating state of the treadmill based on the treadmill control policy.

12. An electronic device, comprising: a memory and a processor, wherein the memory stores a computer program, and the processor is configured to implement a treadmill control method when executing the computer program;

the treadmill control method is configured to control a treadmill equipped with a smart wearable device, the treadmill control method comprises:

obtaining training objective information, user health data, and static physiological data of a target user;

collecting, by the smart wearable device, dynamic physiological data of the target user;

generating instructional language based on the training objective information, the user health data, the static physiological data, and the dynamic physiological data to obtain a natural language instruction;

performing, by a pre-adapted target large language model, inferencing and parsing of the natural language instruction to obtain user profile parsing information;

generating, by a pre-trained decision-making agent, a treadmill control policy adapted to the target user based on the user profile parsing information; and controlling an operating state of the treadmill based on the treadmill control policy.

13. A non-transitory computer-readable storage medium, wherein the computer-readable storage medium stores a program, and the program is executed by a processor to implement a treadmill control method, the treadmill control method is configured to control a treadmill equipped with a smart wearable device, the treadmill control method comprises:

obtaining training objective information, user health data, and static physiological data of a target user;

collecting, by the smart wearable device, dynamic physiological data of the target user;

generating instructional language based on the training objective information, the user health data, the static physiological data, and the dynamic physiological data to obtain a natural language instruction;

performing, by a pre-adapted target large language model, inferencing and parsing of the natural language instruction to obtain user profile parsing information;

generating, by a pre-trained decision-making agent, a treadmill control policy adapted to the target user based on the user profile parsing information; and controlling an operating state of the treadmill based on the treadmill control policy.

* * * * *